(12) United States Patent
Wieland et al.

(10) Patent No.: US 11,253,303 B2
(45) Date of Patent: Feb. 22, 2022

(54) ORTHOPEDIC LOCKING SCREW

(71) Applicant: Stryker European Operations Holdings LLC, Kalamazoo, MI (US)

(72) Inventors: Manfred Wieland, Kiel (DE); Nils Zander, Eckernförde (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 78 days.

(21) Appl. No.: 16/465,805

(22) PCT Filed: Dec. 2, 2016

(86) PCT No.: PCT/IB2016/057304
§ 371 (c)(1),
(2) Date: May 31, 2019

(87) PCT Pub. No.: WO2018/100418
PCT Pub. Date: Jun. 7, 2018

(65) Prior Publication Data
US 2019/0314073 A1    Oct. 17, 2019

(51) Int. Cl.
*A61B 17/86* (2006.01)
*A61B 17/72* (2006.01)
*A61B 17/74* (2006.01)

(52) U.S. Cl.
CPC ........ *A61B 17/8625* (2013.01); *A61B 17/725* (2013.01); *A61B 17/8605* (2013.01); *A61B 17/748* (2013.01); *A61B 2017/8655* (2013.01)

(58) Field of Classification Search
CPC .............. A61B 17/8625; A61B 17/863; A61B 17/72–7291
See application file for complete search history.

(56) References Cited

U.S. PATENT DOCUMENTS

| 2002/0045900 | A1  | 4/2002  | Harder et al. |
| 2004/0127898 | A1* | 7/2004  | Adam ............... A61B 17/72 606/64 |
| 2005/0055024 | A1  | 3/2005  | James et al. |
| 2006/0241604 | A1* | 10/2006 | Frigg ............... A61B 17/744 606/62 |
| 2008/0249580 | A1* | 10/2008 | Evans ............... A61B 17/744 606/86 R |

(Continued)

FOREIGN PATENT DOCUMENTS

WO    2015068027 A2    5/2015

OTHER PUBLICATIONS

International Search Report for PCT/IB2016/057304 dated Mar. 24, 2017.

*Primary Examiner* — Matthew J Lawson
(74) *Attorney, Agent, or Firm* — Lerner, David, Littenberg, Krumholz & Mentlik, LLP

(57) ABSTRACT

The invention relates to an orthopedic locking screw, an orthopedic locking system, and a method for manufacturing an orthopedic locking screw. The orthopedic locking screw may be used for locking an intramedullary nail. The orthopedic locking screw comprises a screw shaft. The screw shaft comprises a recess. The recess extends at least partially along a longitudinal axis of the screw shaft. The recess extends at least partially along a chord of a cross section of the screw shaft. A surface of a circular segment comprising the chord is at least partially provided with a threaded portion.

15 Claims, 5 Drawing Sheets

(56) References Cited

U.S. PATENT DOCUMENTS

| | | | |
|---|---|---|---|
| 2012/0059428 A1* | 3/2012 | Epperly | A61B 17/7233 606/310 |
| 2012/0191092 A1* | 7/2012 | Buettler | A61B 17/8891 606/64 |
| 2013/0041414 A1* | 2/2013 | Epperly | A61B 17/8872 606/310 |
| 2013/0317503 A1* | 11/2013 | Songer | A61B 17/8635 606/66 |
| 2014/0214098 A1* | 7/2014 | Probe | A61B 17/8685 606/306 |

* cited by examiner

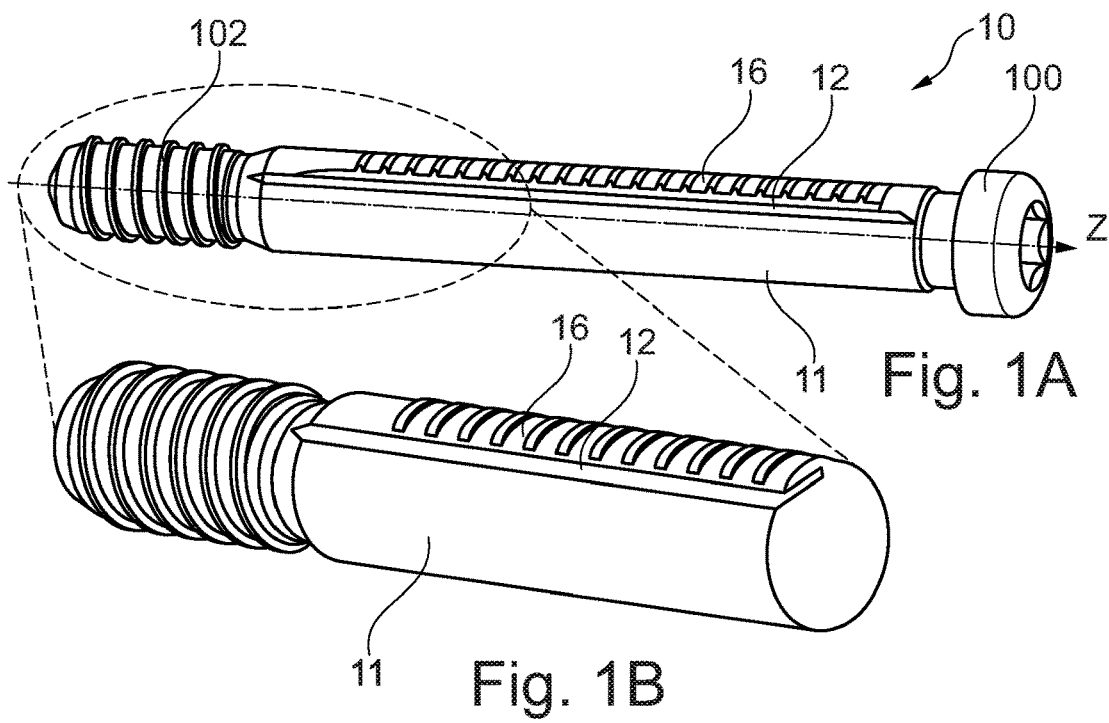
Fig. 1A
Fig. 1B
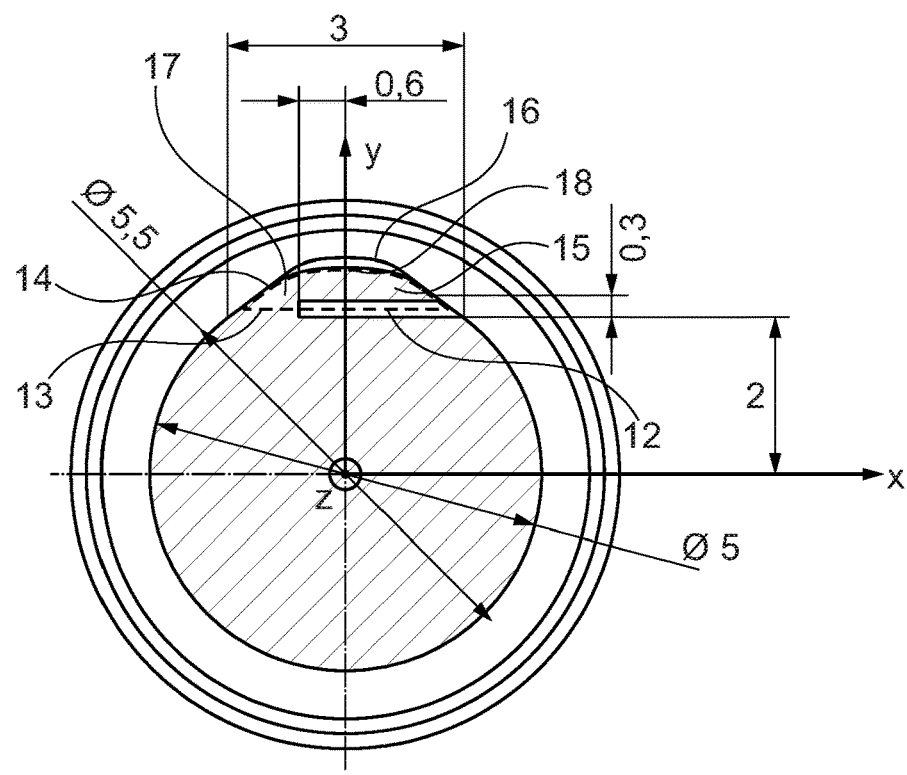
Fig. 2

ORTHOPEDIC LOCKING SCREW

CROSS-REFERENCE TO RELATED APPLICATION

The present application is a national phase entry under 35 U.S.C. § 371 of International Application No. PCT/IB2016/057304, filed Dec. 2, 2016, published as WO 2018/100418, which is hereby incorporated herein by reference.

The invention relates to an orthopedic locking screw, an orthopedic locking system, and a method for manufacturing an orthopedic locking screw. The orthopedic locking screw may be used for locking an intramedullary nail.

BACKGROUND OF THE INVENTION

In general, the intramedullary nail may be for example a femur nail, a humerus nail or a tibia nail. Usually, a leading end portion of the intramedullary nail which may at first be introduced into a medullary channel of a bone comprises two or more through holes adapted to receive locking screws.

At present, inserting locking screws in holes formed in the leading end of implanted intramedullary nails is problematic, namely because of the amount of radiation required during the determination of the position and orientation of transverse locking holes. Furthermore, it is time consuming and ideally requires well-trained and experienced personal. Therefore, it has a significant influence of the overall operation room time required.

Currently, locking of the leading end portion of an intramedullary nail is performed mostly freehand, by inserting a first locking screw into and through a first through hole. Due to the fact that the insertion is difficult to perform, the locking screw may not exactly hit the through hole so that the intramedullary nail may be slightly displaced or even deformed to accommodate the locking screw extending through the through hole. However, this first locking screw will be able to move relative to the intramedullary nail when forces are applied on the nail and screw.

For a locking providing angular stability, a second locking screw may be inserted through a second through hole adjacent the first hole. Also the second locking screw may not exactly hit the second through hole. Accordingly, the second locking screw has to be urged through the hole, with the result that the combination of the first and second locking screws will provide an angle-stable fixation of the intramedullary nail, i.e. a fixation with no movement of a screw relative to the nail.

However, such a fixation of an intramedullary nail requires the insertion of two screws, wherein each insertion of a screw through the leading end portion of an intramedullary nail is difficult and thus time consuming.

BRIEF SUMMARY OF THE INVENTION

Accordingly, there may be need to make a locking of fixation means, as e.g. intramedullary nails, easier. In general, it is of interest to shorten the operation room time which is beneficial not only for the patient under anesthesia, but ultimately reduces costs.

The mentioned aspects are solved by the subject-matter of each of the independent claims. Further embodiments are described in the respective dependent claims.

According to a first aspect of the invention, an orthopedic locking screw is provided. The orthopedic locking screw preferably comprises a threaded leading end, a screw shaft and a head. The screw shaft comprises a longitudinally extending slot or recess. The slot or recess extends at least partially along a longitudinal axis of the screw shaft. The longitudinal axis of the screw shaft may correspond to a Z-axis of the locking screw. The recess further extends into the screw shaft at least partially along a chord of a cross section of the screw shaft. The chord may correspond to an X-axis of the locking screw offset and in particular perpendicular to the Z-axis. A surface of a circular segment outwardly of the slot or recess comprising the chord is at least partially provided with a threaded portion.

The orthopedic locking screw according to the invention allows an easier (self)locking of a fixation means (e.g. an intramedullary nail). Thereby, it may shorten operation room time and reduce costs.

The surface of the circular segment is to be understood as outer edge of the circular segment. The surface can be a circular arc but may also be at least partially flattened or angled.

According to an example, the slot or recess extends only partially along the chord of the cross section of the screw shaft. The recess thereby forms a groove or a blind slot with a longitudinal extension. According to an example, the slot or recess extends along between 90 and 60% of the entire chord length across the cross section of the screw shaft. Preferably, the slot or recess extends along between 80 and 70% of the chord of the cross section of the screw shaft. The recess may be a slot-like cut preferably having parallel flat walls extending along the chord with the recess being spaced apart from the longitudinal axis Z of the screw.

However, the slot or recess may also extend along the entire chord of the cross section of the screw shaft and thereby form a through hole or passage. The recess then separates a cylinder segment from the screw shaft which may only be connected with the screw shaft at one or both ends, i.e., adjacent the head and/or threaded leading end.

According to an example, the screw shaft in the cross section further comprises a bulge arranged between the circular arc of the screw shaft outer circumference and the slot or recess. The threaded portion is arranged on the bulge in the circumference of the bone screw. The bulge can be best understood on basis of its manufacture. A screw shaft with a first diameter of e.g. 5.5 mm may be provided. The threaded portion may be applied to the circumference of the screw shaft. The screw shaft may then be machined or processed in all portions of the circumference, which not provided with a threaded portion, to a second, smaller diameter of e.g. 5 mm. In other words, the diameter of the screw shaft in the region of the bulge is greater than a diameter of the screw shaft the in the non-threaded area of the screw shaft. As a result, the cross section of the screw shaft is not circular, but eccentric having a bulge. The bulge region of the threaded portion is thereby adopted to engage a smaller diameter bore in a bone nail and cause the shaft segment to deflect towards the longitudinal axis of the screw shaft.

According to an example, the recess is arranged between the circular arc and the longitudinal axis of the screw shaft, when seen in the cross section in a direction perpendicular to the chord. The direction perpendicular to the chord may correspond to a Y-axis of the locking screw offset and in particular perpendicular to the X- and Z-axes. According to an example, the recess may be arranged closer to the circular arc than to the longitudinal axis of the screw shaft. Preferably, the recess may be arranged in an upper third or fourth of a distance between an upper reference at the circular arc and a lower reference at the longitudinal axis of the screw shaft. The recess may be asymmetrically arranged relative to the Y-axis perpendicular to the chord.

However, the recess may also be arranged in a centre of the screw shaft along the longitudinal axis Z of the screw shaft.

According to an example, the slot or recess has its opening and thereby its orientation in a direction opposite to a rotation direction of the orthopedic locking screw or the screw shaft. So, for a right-hand thread, the opening of the recess is on the left side and vice versa. As a result, a turning in of the screw shaft leads to a closing and not to an opening of the recess.

According to an example, the recess is a slot-like cut out. The recess may be cut into the screw shaft by e.g. mechanical or laser cutting.

According to an example, the threaded shaft portion is only provided on the circular arc of the circular shaft segment outwardly of the chord. This means no other circumferential parts of screw shaft are threaded (except for the threaded leading end of the screw). In other words, the circular arc of the screw shaft comprising the chord is provided with a partial thread. The parts of screw shaft outside the circular arc have a smooth surface.

In contrast, one or more additional threaded portions may be provided on portions of the screw shaft adjacent to the circular segment and/or on a portion of the screw shaft directly opposite to the circular segment comprising the chord. The additional threaded portion may also cover the entire circumference of the screw shaft. The additional threaded portion may but also may not have the same thread characteristics as the threaded portion provided on the circular arc of the circular segment comprising the chord.

According to an example, the, in the cross section of the screw shaft, circular segment comprising the chord and the circular arc essentially forms a deformable or deflectable element. The deformable element is deformable relative to the screw shaft. In a 3D or plan view, the deformable element has essentially a shape of a cylinder segment of the screw shaft. The threaded arcuate portion deflects towards the centre of the screw, thus closing the recess or slot during insertion into the bone in the intramedullary nail.

According to an example, the deflectable or deformable element is elastically deformable. The deformable element may also be plastically deformable.

A second aspect of the invention relates to an orthopedic locking system. The orthopedic locking system comprises an orthopedic locking screw having a shaft as described above and an intramedullary nail. A threaded portion of the orthopedic locking shaft screw is configured to be fastened in a threaded bore arranged in the intramedullary nail. The threaded bore may be arranged at a distal end of the intramedullary nail.

Although a screw may be a preferred locking member, also a bolt or nail may be use as locking member. The intramedullary nail may be any kind of fixation means.

The thread of the threaded bore in the intramedullary nail may have a height in a range of 0.1 to 0.3 mm for a bore with a diameter of 5 mm. It may be configured to allow just an engagement with the threaded portion of the orthopedic locking screw shaft, but does not (negatively) influence the stiffness and strength of the intramedullary nail.

According to an example, a pitch of the threaded portion of the orthopedic locking screw corresponds to a pitch of the threaded bore in the intramedullary nail.

According to an example, the recess or slot is configured for compensating manufacturing tolerances of the orthopedic locking screw, the intramedullary nail and/or the bore arranged in the intramedullary nail.

According to an example, the orthopedic locking screw shaft and the intramedullary nail are configured for an angularly stable connection.

A third aspect of the invention relates to a method for manufacturing an orthopedic locking screw. It comprises the following steps, not necessarily in this order:
  providing a screw comprising a screw shaft,
  forming a recess or slot in the screw shaft, wherein the recess extends at least partially along a longitudinal axis of the screw shaft and partially along a chord of a cross section of the screw shaft, and
  forming a threaded portion at least partially in a circular arc of a circular segment comprising the chord.

According to an example, the recess extends only partially along the chord of the cross section of the screw shaft. According to an example, the threaded portion is only provided on the circular arc of the circular segment and located radially outwardly from the longitudinal screw axis comprising the chord.

Step S3 may also be implemented before step S2 in that the threaded portion is formed in an area corresponding to a future circular arc of a future circular segment comprising the chord to be formed afterwards.

It shall be understood that the orthopedic locking screw, the orthopedic locking system, and the method for manufacturing an orthopedic locking screw according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings:

FIG. 1A shows a 3D view of an orthopedic locking screw according to the invention and FIG. 1B shows an enlarged detail of the 3D view.

FIG. 2 shows a recess and a chord in a cross section of a screw shaft.

DETAILED DESCRIPTION

Figure 3A:
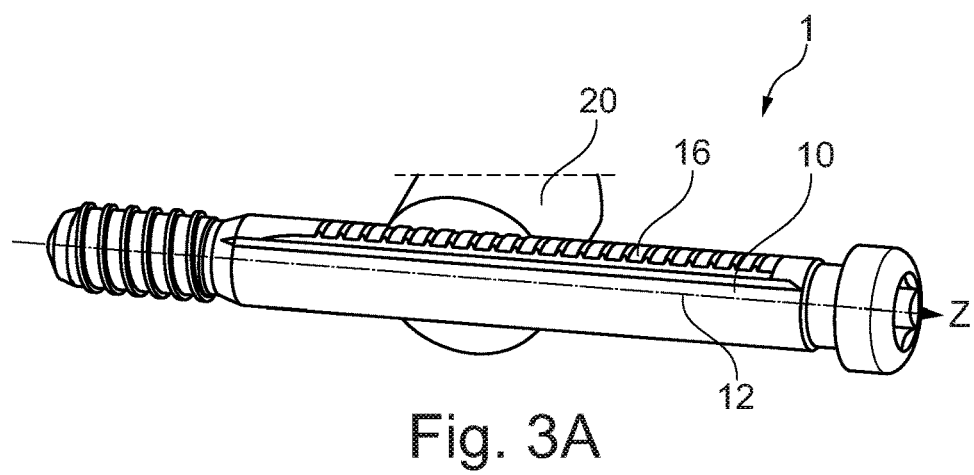
FIGS. 3A and 3B shows two 3D views of an orthopedic locking system according to the invention.

FIG. 1A shows a 3D view of an orthopedic locking screw 10 according to the invention and FIG. 1B shows an enlarged detail of the 3D view. The orthopedic locking screw 10 comprises a screw shaft 11, a head 100 and a threaded leading end 102. The screw shaft 11 comprises a recess 12. The recess 12 is a slot-like cut out. The recess 12 extends partially along a longitudinal axis Z of the screw shaft 11. The recess 12 extends partially along a chord 13 of a cross section of the screw shaft 11. The recess 12 thereby forms a groove or a blind slot with a longitudinal extension along the longitudinal axis Z of the screw shaft 11.

FIG. 2 shows the cross section of the screw shaft 11. The cross section shows the recess 12 or slot and the chord 13 of the screw shaft 11. The chord 13 extends parallel to an X-axis of the locking screw perpendicular to the Z-axis. A surface 14 of a circular segment 15 comprising the chord 13 is provided with a threaded portion 16. Only the surface or circular arc 14 of the circular segment 15 comprising the chord 13 is provided with threads. No other parts of screw shaft 11 are threaded, in contrast, the parts of screw shaft 11 outside the circular arc 14 of the circular segment 15 have a smooth surface.

The recess 12 is arranged between the outer surface of circular arc 14 and the longitudinal axis Z of the screw shaft 11, when seen in the cross section in a direction perpendicular to the chord 13. The direction perpendicular to the chord 13 corresponds to a Y-axis of the locking screw. The recess 12 is here arranged closer to the circular arc 14 than to the longitudinal axis Z of the screw shaft 11. In particular, the recess or slot 12 is arranged in an upper third or fourth of a distance between the circular arc 14 as upper reference and the longitudinal axis Z of the screw shaft 11 as lower reference. The diameter of threaded leading end 104 is 5 mm and the pitch of its threads here equals the pitch of threads 16.

In FIG. 2, the screw shaft 11 has a diameter of about 5 mm. The recess 12 has a distance of about 2 mm from the center or the longitudinal axis Z of the screw shaft 11. The recess 12 preferably has a height of 0.3 mm. The recess 12 extends along between 90 and 60% of the length of the chord 13 of the cross section of the screw shaft 11 and here to a depth of about 2.1 mm. The screw shaft 11 in the cross section further comprises a bulge 18 arranged between the circular arc 14 and the recess 11. The diameter of the screw shaft at an apex of the bulge 18 is 5.5 mm. The threaded portion 16 is arranged on the bulge 18.

Figure 3B:
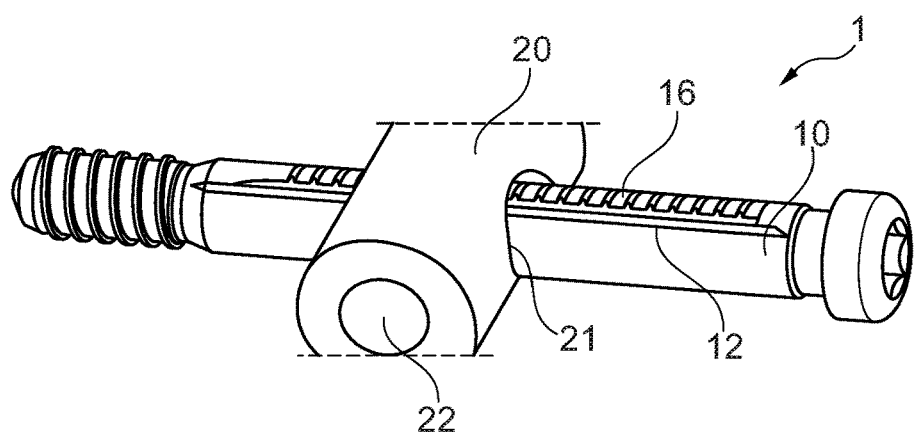

FIGS. 3A and 3B show two 3D views of an orthopedic locking system 1 according to the invention. The orthopedic locking system 1 comprises the orthopedic locking screw 10 as described above and an intramedullary nail 20. The intramedullary nail 20 has a non-threaded bore 22 and a threaded cross bore 21 for the orthopedic locking screw 10. The orthopedic locking screw 10 comprises the screw shaft 11 with the recess slot 12. The recess 12 extends partially along the longitudinal axis Z of the screw shaft 11 and partially along the chord 13 of the cross section of the screw shaft 11. The circular arc 14 of the circular segment 15 comprising the chord 13 shows the threaded portion 16 which engages in the threaded bore 21 of the intramedullary nail 20.

The recess or slot 12 of the screw shaft 11 is dimensioned for compensating manufacturing tolerances of the orthopedic locking screw 10, the intramedullary nail 20 and the bore arranged in the intramedullary nail 20. The orthopedic locking screw 10 and the intramedullary nail 20 form an angularly stable connection.

Figure 4:
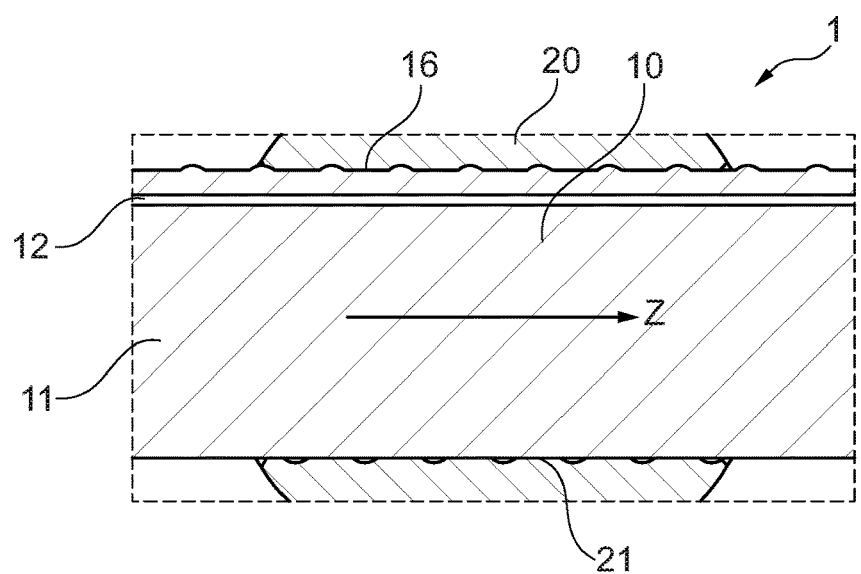
FIG. 4 is a cross section showing a threaded portion of an orthopedic locking screw fastened in a threaded bore arranged in an intramedullary nail.

FIG. 4 is a cross section showing the threaded shaft portion 16 of the orthopedic locking screw 10 fastened in the threaded bore 21 arranged in the intramedullary nail 20. A pitch of the threaded portion 16 of the orthopedic locking screw 10 corresponds here to a pitch of the threaded bore 21 in the intramedullary nail 20. The circular segment 15 comprising the chord 13 and the circular arc 14 essentially forms an elastically deformable element 17.

Figure 5:
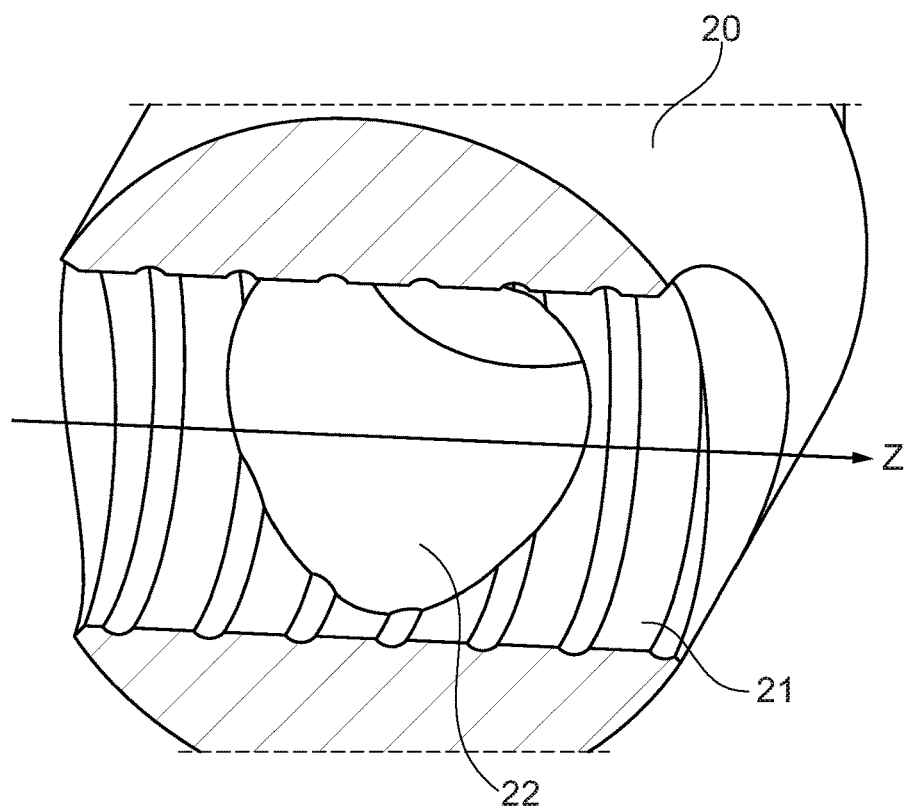
FIG. 5 shows a 3D view of a cut through an intramedullary nail.

FIG. 5 shows a 3D view of a cut through the intramedullary nail 20. The intramedullary nail 20 shows the threaded bore 21 along the longitudinal axis Z of the screw shaft 11 of the locking screw (not shown) and a non-threaded bore 22 along a longitudinal axis of the intramedullary nail 20. The longitudinal axis Z of the screw shaft 11 of the locking screw and the longitudinal axis of the intramedullary nail 20 may be transverse in the meaning of non-perpendicular to each other.

Figure 6:
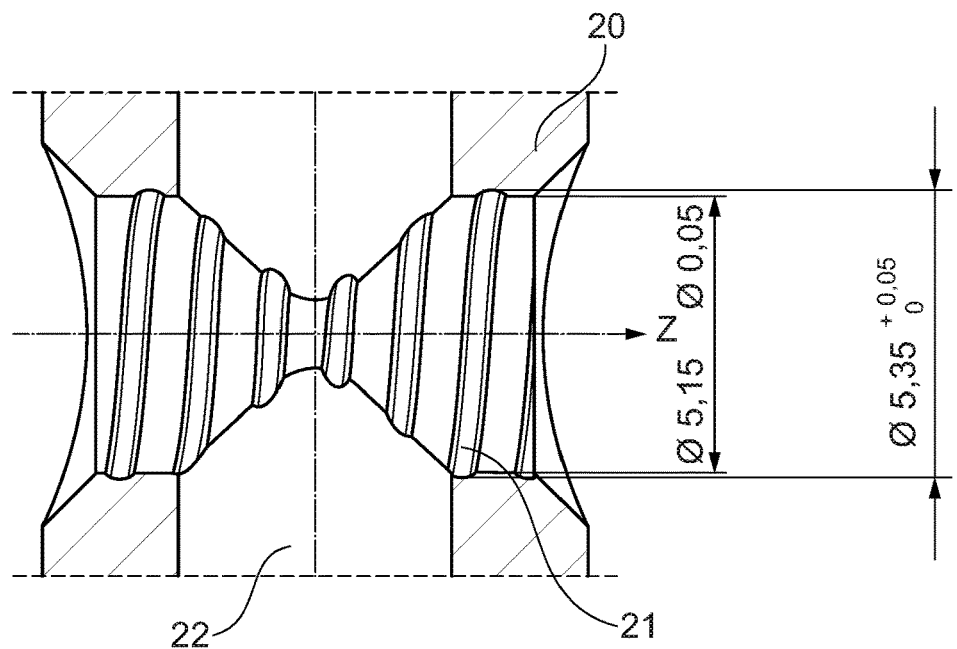
FIG. 6 shows a cross section through an intramedullary nail.

FIG. 6 shows a cross section through the intramedullary nail 20. As shown in FIG. 4, the intramedullary nail 20 shows the threaded bore 21 along the longitudinal axis Z of the screw shaft 11 of the locking screw (not shown) and a non-threaded bore 22 along a longitudinal axis of the intramedullary nail 20. The longitudinal axis Z of the screw shaft 11 of the locking screw and the longitudinal axis of the intramedullary nail 20 are transverse in the meaning of non-perpendicular to each other. The thread of the threaded bore 21 has a major diameter of 5.35 mm and a minor diameter of 5.15 mm.

Figure 7A:
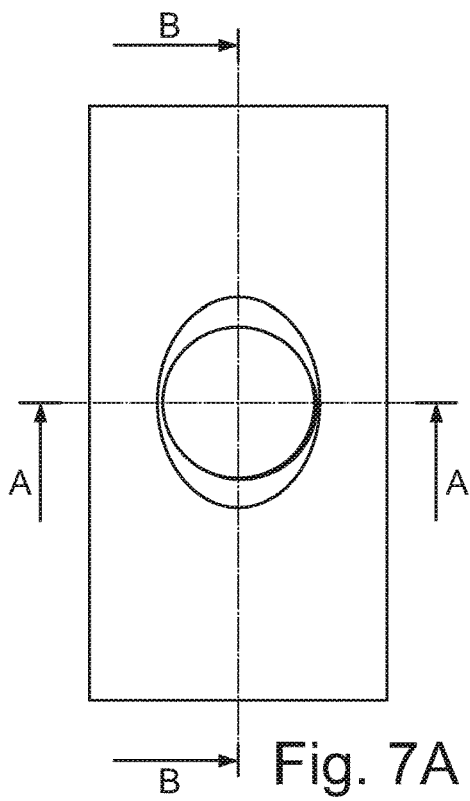
FIG. 7A shows a side view of the intramedullary nail for use with the locking screw.
Figure 7B:
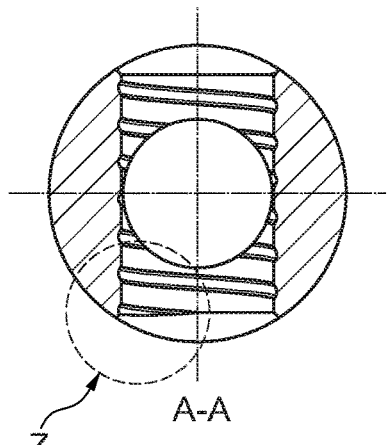
FIG. 7B shows a cross-section of FIG. 7A along lines A-A.
Figure 7D:
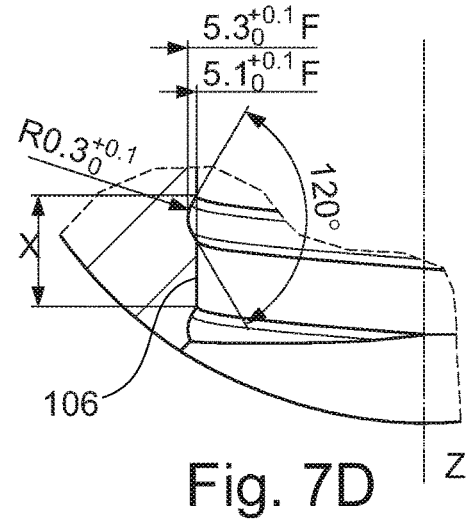
FIG. 7D shows an enlarged view of area Z of FIG. 7B.
Figure 7C:
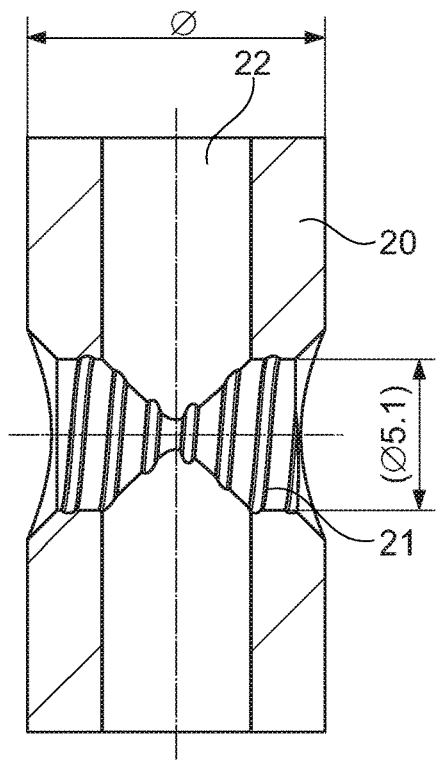
FIG. 7C shows a cross-section of FIG. 7A along lines B-B.
Figure 7E:
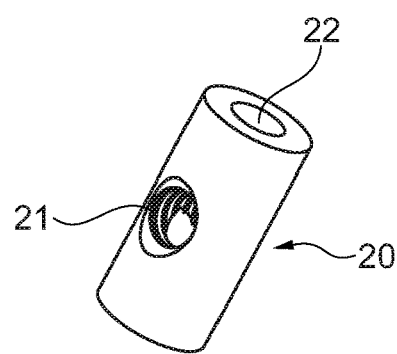
FIG. 7E shows an isomeric view of the nail of FIG. 7A.

FIGS. 7A-7E shows further views of the intramedullary nail 20 comprising the threaded bore 21 and the non-threaded bore 22. FIG. 7D shows details of the thread of the threaded bore 21. The thread of the threaded bore 21 in the intramedullary nail 20 has a height of 0.2 mm, a radius of 0.3 mm and opens to 120°. It allows an engagement with the threaded portion 16 of the orthopedic locking screw 10, but does not weaken the intramedullary nail 20. As the orthopedic locking screw 10 is inserted into the threaded bore 21, the outer surface of the circular segment 15 contacts a segment 106 of the threaded bore 21 and deflects inwardly to close the slot or recess 12. Thus, the circular segment 15 is able to deflect or deform inwardly at least partially to provide an elastic force for holding the orthopedic locking screw 10 in a desired axial and/or angular position.

Figure 8:
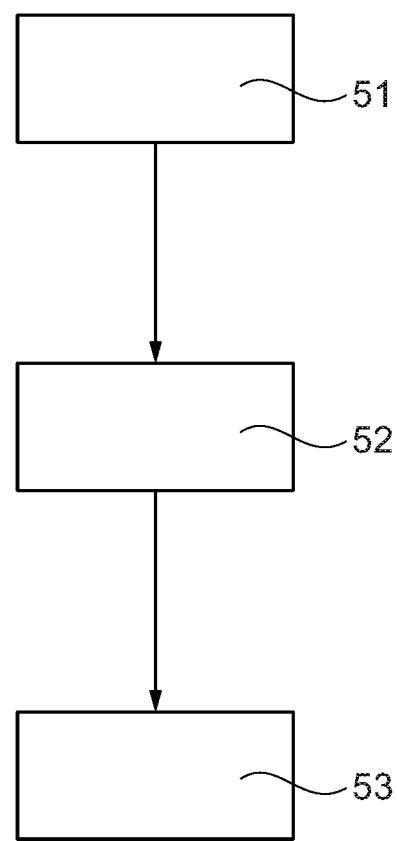
FIG. 8 shows a method for manufacturing an orthopedic locking screw according to the invention.

FIG. 8 shows a method for manufacturing an orthopedic locking screw 10 according to the invention. It comprises the following steps:

In a step S1, providing a screw comprising a screw shaft 11.

In a step S2, forming a recess 12 in the screw shaft 11, wherein the recess 12 extends at least partially along a longitudinal axis Z of the screw shaft 11 and a chord 13 of a cross section of the screw shaft 11.

In a step S3, forming a threaded portion 16 at least partially in a circular arc 14 of a circular segment 15 comprising the chord 13.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An orthopedic locking screw,
wherein the orthopedic locking screw comprises a screw shaft having an outer surface circumscribing an interior volume,
wherein the screw shaft comprises a slot extending into the screw shaft,
wherein the slot defines an opening along the outer surface of the screw shaft, the opening having a length dimension extending at least partially along a longitudinal axis of the screw shaft,
wherein the slot has a depth dimension extending from the opening into the interior volume of the screw shaft along a chord of a cross section of the screw shaft the cross section being oriented orthogonally to the longitudinal axis of the screw shaft, the slot defined by opposing planar surfaces extending within the interior volume of the screw shaft from the opening to a blind end opposite to the opening along the depth dimension, the opposing planar surfaces of the slot extending a distance along the depth dimension between 90 and 60% of the length of the chord, and
wherein an arcuate portion of the outer surface defined between opposing ends of the chord is at least partially provided with a threaded portion.

2. Orthopedic locking screw according to claim 1, wherein the screw shaft in the cross section further comprises a bulge arranged between the outer surface and the slot, and wherein the threaded portion is arranged on the bulge.

3. Orthopedic locking screw according to claim 2, wherein a diameter of the screw shaft in a region of the bulge is greater than a diameter of the screw shaft in a non-threaded area of the screw shaft.

4. Orthopedic locking screw according to claim 1, wherein the slot is arranged, when seen in the cross section, between the outer surface and the longitudinal axis of the screw shaft.

5. Orthopedic locking screw according to claim 1, wherein the slot is arranged, when seen in the cross section, closer to the outer surface than to the longitudinal axis of the screw shaft.

6. Orthopedic locking screw according to claim 1, wherein the threaded portion is only provided on the arcuate portion of the outer surface defined between the opposing ends of the chord.

7. Orthopedic locking screw according to claim 1, wherein a segment of the screw shaft defined between the arcuate portion of the outer surface and the chord forms a deformable element.

8. Orthopedic locking screw according to claim 7, wherein the deformable element is elastically deformable.

9. An orthopedic locking system, comprising:
an orthopedic locking screw according to claim 1, and
an intramedullary nail,
wherein a threaded portion of the orthopedic locking screw is configured to be fastened in a threaded bore arranged in the intramedullary nail.

10. Orthopedic locking system according to claim 9, wherein a pitch of the threaded portion of the orthopedic locking screw corresponds to a pitch of the threaded bore in the intramedullary nail.

11. Orthopedic locking system according to claim 9, wherein the slot is configured to compensate for manufacturing tolerances of the orthopedic locking screw, the intramedullary nail and/or the bore arranged in the intramedullary nail.

12. Orthopedic locking system according to claim 9, wherein the orthopedic locking screw and the intramedullary nail are configured for an angularly stable connection.

13. A method for manufacturing an orthopedic locking screw, comprising the following steps:
providing a screw comprising a screw shaft having an outer surface circumscribing an interior volume,
forming a slot extending into the screw shaft, wherein the slot defines an opening along the outer surface of the screw shaft, the opening having a length dimension extending at least partially along a longitudinal axis of the screw shaft, and the slot has a depth dimension extending from the opening into the interior volume of the screw shaft along a chord of a cross section of the screw shaft, the cross section being oriented orthogonally to the longitudinal axis of the screw shaft, the slot defined by opposing planar surfaces extending within the interior volume of the screw shaft from the opening to a blind end opposite to the opening along the depth dimension, the opposing planar surfaces of the slot extending a distance along the depth dimension between 90 and 60% of the length of the chord, and
forming a threaded portion at least partially along an arcuate portion of the outer surface of the screw shaft, the arcuate portion defined between opposing ends of the chord.

14. An orthopedic locking screw,
wherein the orthopedic locking screw comprises a screw shaft having an outer surface circumscribing an interior volume,
wherein the screw shaft has a slot formed therein,
wherein the slot defines an opening along the outer surface of the screw shaft, the opening having a length dimension extending at least partially along a longitudinal axis of the screw shaft, and the slot has a depth dimension extending from the opening into the interior volume of the screw shaft along a chord of a cross section of the screw shaft, the cross section being oriented orthogonally to the longitudinal axis of the screw shaft and the chord being offset from the longitudinal axis, and wherein the slot is defined by opposing planar surfaces extending within the interior volume of the screw shaft from the opening to a blind end opposite to the opening along the depth dimension, the opposing planar surfaces of the slot extending a distance along the depth dimension between 90 and 60% of the length of the chord, the chord forming a shaft segment having an arcuate outer surface, wherein the arcuate outer surface of the segment is at least partially provided with a threaded portion, a peak of the threaded portion having a first radial distance from the longitudinal axis that is greater than a second radial distance from the longitudinal axis of a surface of a non-threaded area of the shaft.

15. Orthopedic locking screw of claim 14, wherein the peak of the threaded portion is adapted to engage a smaller diameter bore in a bone nail and cause the shaft segment to deflect towards the axis.

\* \* \* \* \*